(12) United States Patent
Tachikawa (10) Patent No.: US 10,568,508 B2
(45) Date of Patent: Feb. 25, 2020

(54) OPHTHALMOLOGIC IMAGING APPARATUS (71) Applicant: CANON KABUSHIKI KAISHA, Tokyo (JP)

(72) Inventor: Hiroto Tachikawa, Fujisawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/881,000

(22) Filed: Oct. 12, 2015

(65) Prior Publication Data

US 2016/0106316 A1   Apr. 21, 2016

(30) Foreign Application Priority Data

Oct. 15, 2014 (JP) .................................. 2014-210837

(51) Int. Cl.
*A61B 3/15* (2006.01)
*A61B 3/12* (2006.01)

(52) U.S. Cl.
CPC ................ *A61B 3/152* (2013.01); *A61B 3/12* (2013.01)

(58) Field of Classification Search
CPC ......... A61B 3/152; A61B 3/0083; A61B 3/12; A61B 3/103; A61B 5/7455; A61B 3/0091; A61B 3/0025; A61B 3/18; A61B 5/7415; A61B 3/145; A61B 3/0041; A61B 3/1015; A61B 2560/0425

USPC .......................... 351/221, 206, 207, 200, 210
See application file for complete search history.

(56) References Cited

U.S. PATENT DOCUMENTS

| | | | | |
|---|---|---|---|---|
| 2004/0004694 A1* | 1/2004 | Sugino | ...................... | A61B 3/14 351/206 |
| 2013/0077047 A1* | 3/2013 | Uchida | ..................... | A61B 3/12 351/206 |

FOREIGN PATENT DOCUMENTS

| JP | 2011-245028 A | | 12/2011 |
|---|---|---|---|
| JP | 2011245028 A | * | 12/2011 |

* cited by examiner

*Primary Examiner* — Stephone B Allen
*Assistant Examiner* — Rahman Abdur
(74) *Attorney, Agent, or Firm* — Canon U.S.A., Inc. IP Division

(57) ABSTRACT

An ophthalmologic imaging apparatus includes a housing configured to include an optical system that irradiates a subject's eye with measurement light and receives returning light returned from the subject's eye irradiated with the measurement light, a rotation unit configured to rotate the housing by making a predetermined position on an optical axis of the optical system as a rotation center, a position changing unit configured to change a position of the rotation center on the optical axis of the optical system, and a holding unit configured to hold a positional relationship between the housing and the subject's eye when the position of the rotation center on the optical axis of the optical system is changed.

16 Claims, 9 Drawing Sheets

D-D CROSS-SECTION

FIG.3B

E-E CROSS-SECTION

OPHTHALMOLOGIC IMAGING APPARATUS

BACKGROUND

Field of the Invention

Aspects of the present invention generally relate to an ophthalmologic imaging apparatus for capturing an image of an eye fundus of a subject's eye.

Description of the Related Art

In an ophthalmologic imaging apparatus such as a scanning laser ophthalmoscope (SLO) or an eye fundus camera, a panning-tilting mechanism for rotating an apparatus main body in an up-down direction and a right-left direction has been known. The panning-tilting mechanism can change an irradiation angle of measurement light with respect to a subject's eye by making an optional point as a rotation center of the apparatus main body. Generally, when an irradiation angle of the measurement light with respect to the subject's eye is changed by making the pupil center of the subject's eye as a rotation center while maintaining an operation distance between an optical system of the apparatus main body and the subject's eye in an appropriate state, peripheral portions in the eye fundus around the central portion thereof can be observed easily in addition to the central portion of the eye fundus. With respect to the above operation, an apparatus that uses a motor to move an apparatus main body including an optical system along an arc-shape guide has been discussed in Japanese Patent Application Laid-Open No. 2011-245028.

Further, in order to capture a desired position in the eye fundus of the subject's eye with unstable visual fixation, the panning-tilting mechanism may be used to adjust an optical axis of the apparatus main body with an axis of the subject's eye (i.e., a straight line that connects a macula of the eye fundus and a gazing object) to make the measurement light pass through the pupil center. At this time, after an examiner has arranged the apparatus main body at an appropriate operation distance from the subject's eye and completed a focus adjustment thereof, the axis of the eye and the optical axis may be misaligned because of fixation disparity arising in the subject's eye. In such a case, the examiner firstly rotates the apparatus main body by the panning-tilting mechanism to make the axis of the eye and the optical axis substantially conform to each other in order to emit the measurement light substantially vertical to the eye fundus of the subject's eye. Then, the examiner places back the apparatus main body to the appropriate operation distance, and moves the apparatus main body in parallel to allow the measurement light pass through the pupil center of the subject's eye.

SUMMARY OF THE INVENTION

According to an aspect of the present invention, an ophthalmologic imaging apparatus includes a housing configured to include an optical system that irradiates a subject's eye with measurement light and receives returning light returned from the subject's eye irradiated with the measurement light, a rotation unit configured to rotate the housing by making a predetermined position on an optical axis of the optical system as a rotation center, a position changing unit configured to change a position of the rotation center on the optical axis of the optical system, and a holding unit configured to hold a positional relationship between the housing and the subject's eye when the position of the rotation center on the optical axis of the optical system is changed.

Further features of the present disclosure will become apparent from the following description of exemplary embodiments with reference to the attached drawings.

DESCRIPTION OF THE EMBODIMENTS

In the conventional ophthalmologic imaging apparatus, an axis of the eye and an optical axis may be misaligned because of fixation disparity arising in the subject's eye. In such a case, a rotation center of an apparatus main body is moved from the pupil center of the subject's eye to the rotation center of the eyeball of the subject's eye through the panning-tilting mechanism. With this operation, even if an examiner does not make an adjustment on an operation distance or a parallel movement, the above-described misalignment can be reduced by rotating the apparatus main body through the panning-tilting mechanism. At this time, because the apparatus main body has to be moved closer to the subject's eye, the apparatus main body may easily be in contact with the subject's face.

Therefore, the exemplary embodiments are directed to an ophthalmologic imaging apparatus capable of switching the rotation centers of the apparatus main body between the pupil center of the subject's eye and the eyeball rotation center of the subject's eye through the panning-tilting mechanism while maintaining an appropriate positional relationship between the subject's eye and the apparatus main body.

First, the ophthalmologic imaging apparatus according to the exemplary embodiments includes a housing for supporting an optical system (e.g., optical system main unit 6) that irradiates the subject's eye with measurement light and receives light returning from the subject's eye irradiated with the measurement light. Herein, the optical system main unit 6 is enclosed within the housing, and capable of integrally moving with the housing.

Further, the ophthalmologic imaging apparatus according to the exemplary embodiments includes a rotation unit for rotating the housing by making a predetermined position on the optical axis of the optical system (e.g., a point "O" on an optical axis of an objective lens 10) as a rotation center. A mechanism (e.g., an arm 4 and an arm holding member 3) that rotates and moves the housing in a right-left direction (i.e., horizontal direction) by making a straight line in a center-of-gravity direction passing through the rotation center as a rotation axis (i.e., shaft 11) can be given as an example of the rotation unit. A user uses the above mechanism to execute an operation generally known as a panning operation. Further, a mechanism (e.g., a pinion gear 8, a rack gear 12, an arc-shape guiding member 5, and a guide block 7) that moves and rotates the housing in an up-down direction (i.e., vertical direction) by making a straight line in a horizontal direction passing through the rotation center as a rotation axis can be given as an example of the rotation unit. The user uses the above mechanism to execute an operation generally known as a tilting operation.

Generally, a rack gear and a pinion gear are used to transmit force acting on a first member to a second member in order to move the second member with respect to the first member, or to maintain or balance a positional relationship between the first member and the second member. In the exemplary embodiments, the rack gear 12 and the pinion gear 8 are used for the latter purpose. More specifically, a force of a spring 14 corresponding to the weight of the optical system main unit 6 acts on the pinion gear 8 in a clockwise direction, and that force is transmitted to the rack gear 12. With the above configuration, the guide block 7 can be suppressed from slipping off from the arc-shape guiding member 5 in the gravitational direction because of the weight of the optical system main unit 6. Further, the guide block 7 disposed at the side of the optical system main unit 6 restricts a movement direction of the optical system main unit 6 with respect to the arc-shape guiding member 5.

Further, the ophthalmologic imaging apparatus according to the exemplary embodiments includes a position changing unit for changing a position of the rotation center of the rotation unit on the optical axis of the optical system. A mechanism for moving the rotation center (e.g., a mechanism for moving a platform 2 in the front-back direction with respect to a base plate 1 by using a linear guide) is given as an example of the position changing unit (see, a first exemplary embodiment). Further, a mechanism for switching a plurality of rotation centers is given as an example of the position changing unit (see, a second exemplary embodiment).

Furthermore, the ophthalmologic imaging apparatus according to the present exemplary embodiments includes a holding unit for holding a positional relationship between the housing and the subject's eye when a position of the rotation center of the rotation unit on the optical axis of the optical system is changed. A mechanism disposed at a position between the housing and the rotation unit, which moves the housing with respect to the rotation unit, is given as an example of the holding unit. For example, a movable plate 9 provided with the guide block 7 and the pinion gear 8, movable with respect to the optical system main unit 6 through linear guides 18a and 18b corresponds to the above-described mechanism. With this mechanism, the movable plate 9 can move in a single axis direction (i.e., substantially optical axis direction) with respect to the optical system main unit 6. At this time, the movable plate 9 is moved to a direction opposite to a direction in which a position of the rotation center is changed (i.e., a direction in which the apparatus main body moves closer to the subject's eye) by an amount of change in the position of the rotation center, so that the operation distance can be maintained at a specific distance even if the position of the rotation center is changed. In other words, even if the position of the rotation center is changed, the user can perform the panning-tilting operation without moving the apparatus main body closer to the subject's eye.

Herein, it is preferable that the holding unit include a driving unit (e.g., a motor 19) for driving the housing in a direction in which a distance between the housing and the subject's eye is changed, and a control unit (e.g., a personal computer (PC) communicably connected to the motor 19) for controlling the driving unit according to the change in the position of the rotation center of the rotation unit. With this configuration, even if the position of the rotation center is changed, a positional relationship between the subject's eye and the apparatus main body can be maintained automatically and appropriately, and thus the usability thereof can be improved.

Further, the ophthalmologic imaging apparatus according to the exemplary embodiments is applicable to any ophthalmologic imaging apparatuses such as an eye fundus camera, an optical coherence tomography (OCT), and a scanning laser ophthalmoscope (SLO). Hereinafter, the exemplary embodiments of the present invention will be described in detail with reference to the appended drawings.

<Mechanism for Moving Rotation Center>

Figure 1:
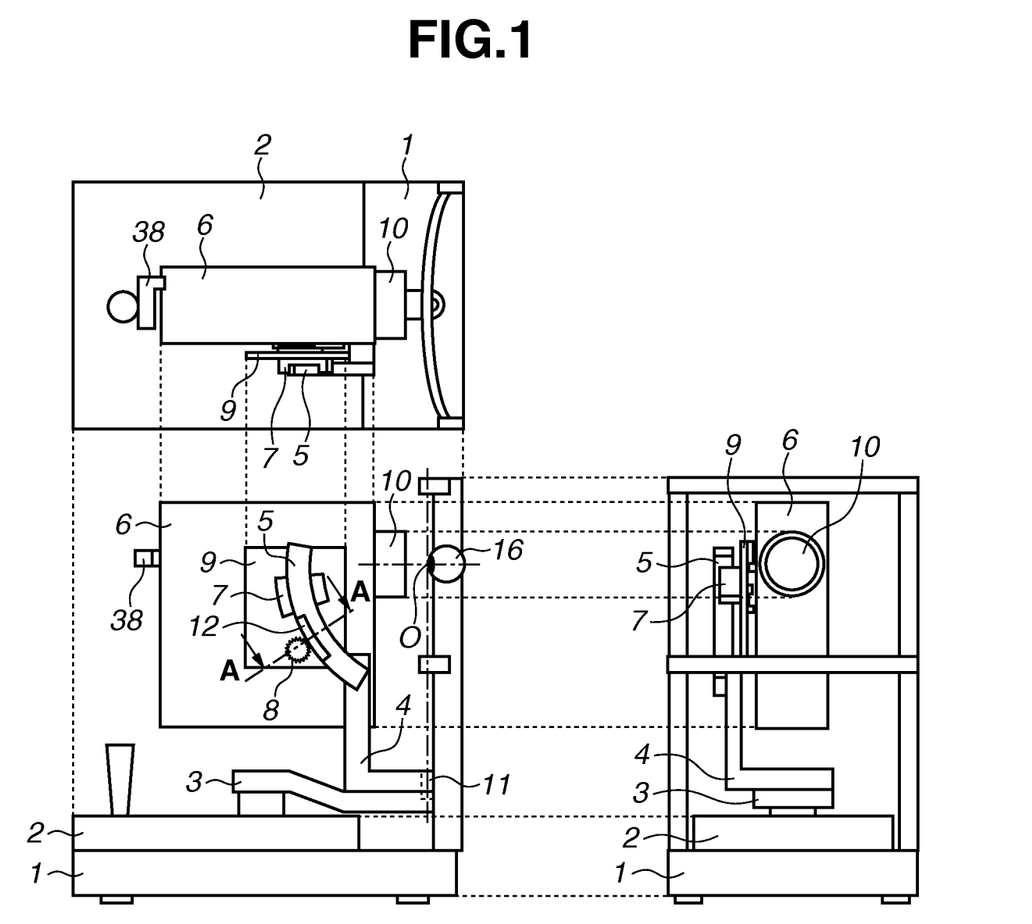
FIG. 1 is a diagram illustrating a configuration of an ophthalmologic imaging apparatus according to a first exemplary embodiment.

First, an SLO as an example of an ophthalmologic imaging apparatus according to a first exemplary embodiment will be described with reference to FIG. 1. FIG. 1 is a diagram illustrating a configuration of the SLO as an example of the ophthalmologic imaging apparatus according to the present exemplary embodiment. The arm holding member 3 is attached to the base plate 1 of the SLO via the platform 2 as an example of the moving unit that moves the rotation center of the apparatus main body. The platform 2 is moved in a front-back direction and a right-left direction (i.e., X-direction and Z-direction) with respect to the base plate 1 through a linear guide, so that relative positions of the subject's eye 16 and the SLO can be changed. The arc-shape guiding member 5 as an example of the rotation unit is fixed to the arm holding member 3 via the arm 4 as an example of the rotation unit. The arc-shape guiding member 5 is a curved guide rail. The optical system main unit 6 is supported by the arc-shape guiding member 5. The optical system main unit 6 is an example of the housing including an optical system that irradiates the subject's eye 16 with measurement light and receives light returning from the subject's eye 16 irradiated with the measurement light. The movable plate 9 as an example of the holding unit, to which the guide block 7 and the pinion gear 8 are attached, is disposed at a side surface of the optical system main unit 6. The rotation center of the arc-shape guiding member 5 is a point O on the optical axis of the objective lens 10 included in the optical system main unit 6, so that an examiner can perform a depression-elevation operation (i.e., tilting operation) to move the optical system main unit 6 in the up-down direction with respect to the rotation center O. The optical system main unit 6 can be rotated and moved within a range of a 15-degree to a 10-degree in the respective directions of up and down directions along the arc-shape guiding member 5 via the guide block 7. The arm 4 is supported by the arm holding member 3 via the shaft 11, so that the examiner can perform a rotation operation (i.e., panning operation) to rotate the optical system main unit 6 about the shaft 11 within a range of an approximately 30-degree in the respective directions of right and left directions. At this time, the examiner can perform the panning-tilting operation of the optical system main unit 6 by holding a handle 38.

Figure 2:
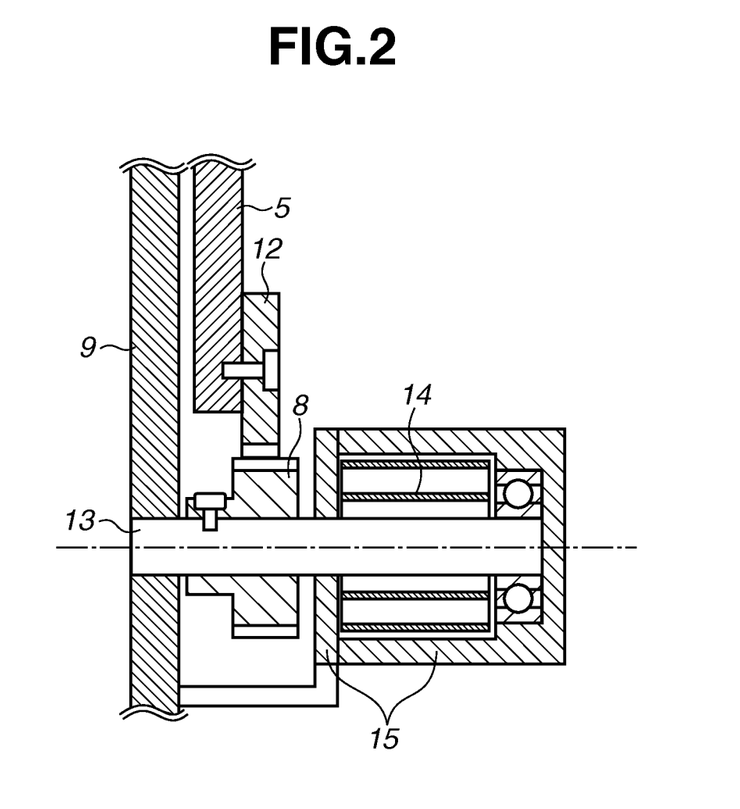
FIG. 2 is a cross-sectional diagram illustrating a balancing mechanism of the ophthalmologic imaging apparatus according to the first exemplary embodiment.

Next, a balancing unit for balancing the own weight of the optical system main unit 6 will be described. FIG. 2 is a cross-sectional diagram taken along a line A-A in FIG. 1. FIG. 2 illustrates the balancing unit for cancelling a lowering force caused by the own weight of the optical system main unit 6. The rack gear 12 is attached to the arc-shape guiding member 5. The rack gear 12 engages with the pinion gear 8 on the outer circumference thereof, and has a shape in which a plurality of gear tooth is arranged in an ark-like state. The pinion gear 8 and the spring 14 are fixed to a rotation shaft 13. One end of the spring 14 is fixed to a spring holder 15 attached to a side surface of the movable plate 9. When the optical system main unit 6 is depressed or elevated, the spring 14 generates a spring force according to a rotation angle of the rotation shaft 13. This spring force offsets the lowering force caused by the own weight of the optical system main unit 6 in a movable range in the up-down direction of the optical system main unit 6. In addition, the spring 14 is a spiral spring also known as a flat spiral spring. Another spring such as a gas spring or a helical extension spring is also applicable to the spring 14 according to the present exemplary embodiment.

Figure 3A:
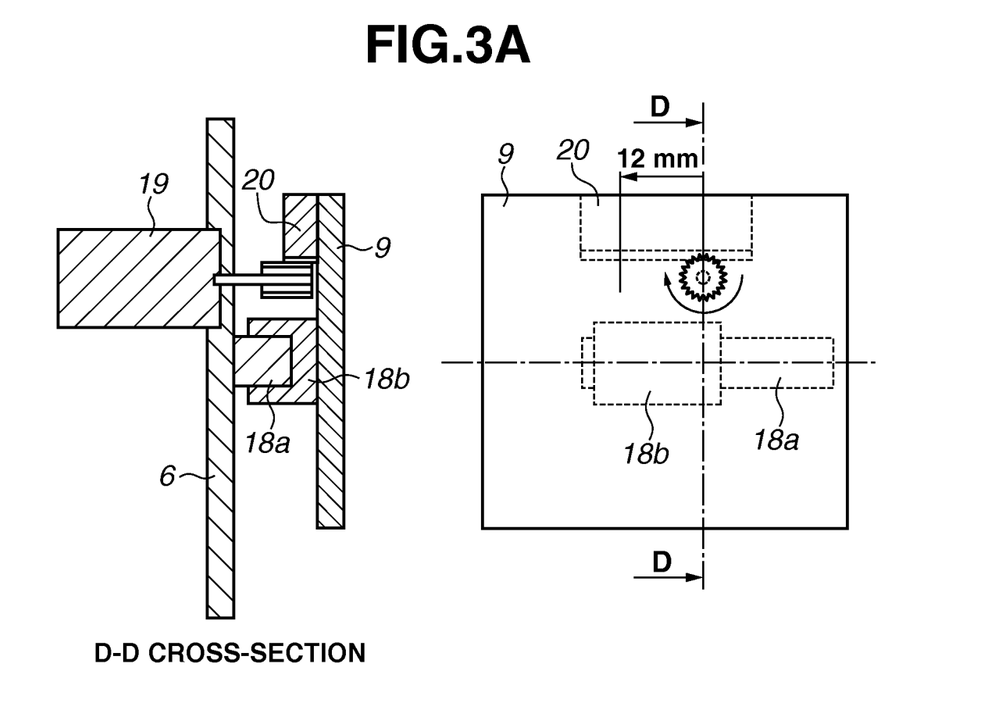
FIGS. 3A and 3B are diagrams illustrating a moving mechanism of an optical system main unit and a movable plate of the ophthalmologic imaging apparatus according to the first exemplary embodiment.
Figure 6A:
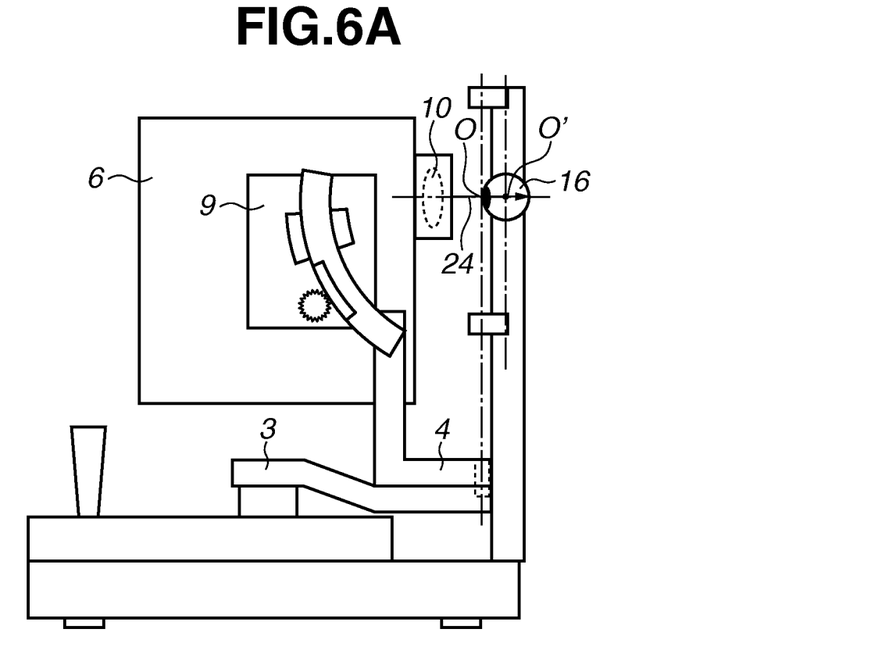
FIGS. 6A and 6B are diagrams illustrating an operation in a pupil center panning-tilting mode of the ophthalmologic imaging apparatus according to the first exemplary embodiment.
Figure 7A:
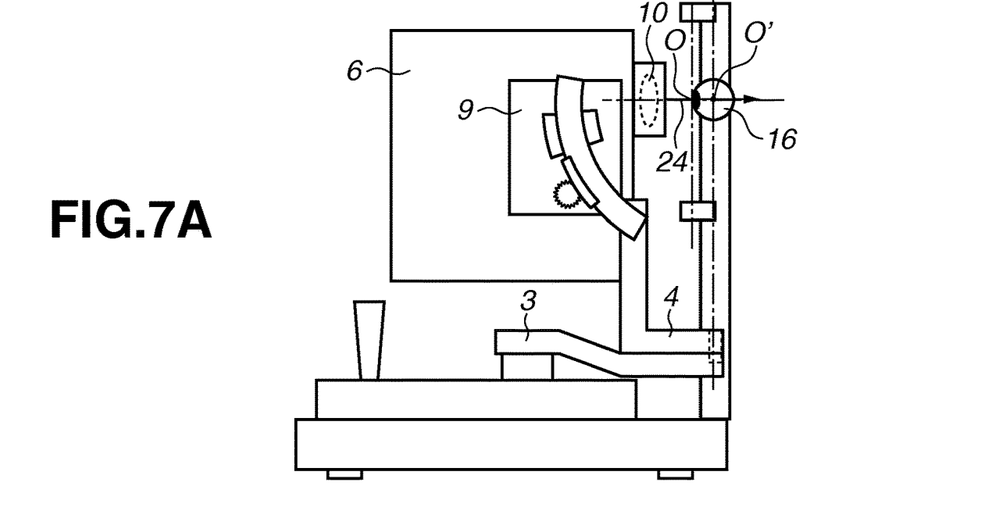
FIGS. 7A, 7B, and 7C are diagrams illustrating an operation in an eyeball rotation center panning-tilting mode of the ophthalmologic imaging apparatus according to the first exemplary embodiment.

A mechanism for moving the optical system main unit 6 and the objective lens 10 with respect to the rotation center of the panning-tilting mechanism will be described. FIG. 3A is a diagram illustrating a mechanism for moving the optical system main unit 6 with respect to the movable plate 9. Operations for relatively moving the optical system main unit 6 and the objective lens 10 with respect to the platform 2 according to the movement of the rotation center of the panning-tilting mechanism are illustrated in the schematic diagrams of FIGS. 6A and 7A. The rotation center of the panning-tilting mechanism is the pupil center O in FIG. 6A, whereas the rotation center thereof is the eyeball rotation center O' in FIG. 7A. The linear guide rail member 18a and the linear guide block member 18b, which constitute the linear guide 18, are fixed to the optical system main unit 6 and the movable plate 9, respectively. The linear guide 18 is arranged in substantially parallel to the optical axis direction of the objective lens 10, so that the optical system main unit 6 can be moved in a substantially same direction as the optical direction. The motor 19 as an example of the driving unit is attached to the side surface of the optical system main unit 6. Further, a rack gear 20 is attached to the movable plate 9. The motor 19 is used to move the optical system main unit 6 with respect to the movable plate 9. The rack gear 20 enables the optical system main unit 6 to move within a movable range of at least 12 mm. This movable range is approximately equal to a distance between the pupil center and the eyeball rotation center of the average human eye. As illustrated in FIGS. 6A and 7A, when the platform 2 is moved to cause the rotation center of the panning-tilting mechanism to move from the pupil center O to the eyeball rotation center O' of the subject's eye 16, the optical system main unit 6 and the objective lens 10 are moved in a direction opposite to the moving direction of the rotation center by a substantially same distance. The moving amount of the platform 2 is monitored and fed back as the moving amount of the optical system main unit 6 caused by the rack gear 20. By offsetting the movement of the platform 2 with the movement of the movable plate 9, a positional relationship between the optical system main unit 6 and the subject's eye 16 can be maintained at an appropriate distance. The optical system main unit 6 may be manually moved with respect to the movable plate 9 without using the motor 19.

Figure 4:
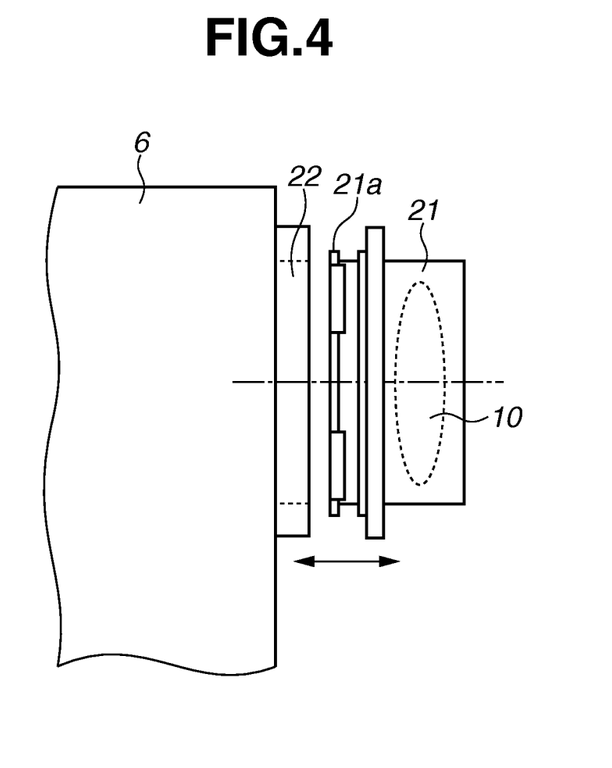
FIG. 4 is a diagram illustrating a coupling portion of an objective lens and the optical system main unit of the ophthalmologic imaging apparatus according to the first exemplary embodiment.

A configuration for switching image capturing modes between a narrow-angle image capturing mode as an example of a first image capturing mode, and a wide-angle image capturing mode as an example of a second image capturing mode will be described with reference to FIG. 4. FIG. 4 is a diagram illustrating a mechanism of a coupling portion of the objective lens 10 and the optical system main unit 6. The objective lens 10 is held by a lens barrel 21. The lens barrel 21 is detachably attached to the optical system main unit 6 so that the examiner can replace the objective lens 10 of a desired projection magnification according to the image-capturing magnification of the SLO. The lens barrel 21 includes a coupling portion 21a for coupling the lens barrel 21 to the optical system main unit 6. Because the coupling portion 21a is configured of a bayonet structure, an electric connection is established when the coupling portion 21a is coupled to the optical system main unit 6 to contact with a connection terminal 21 of the optical system main unit 6. With this electric connection, the control unit can identify a type of the objective lens 10 attached thereto. A narrow-angle lens for capturing a narrow region of the eye fundus at high precision and a wide-angle lens for capturing a wide region thereof are used as the objective lens 10. The examiner can use the respective lenses to selectively operate in a narrow-angle image capturing mode or a wide-angle image capturing mode. In addition, the examiner may switch view angles by changing a scanning quantity of a scanner (not illustrated) that scans the subject's eye 16 with laser.

Figure 5A:
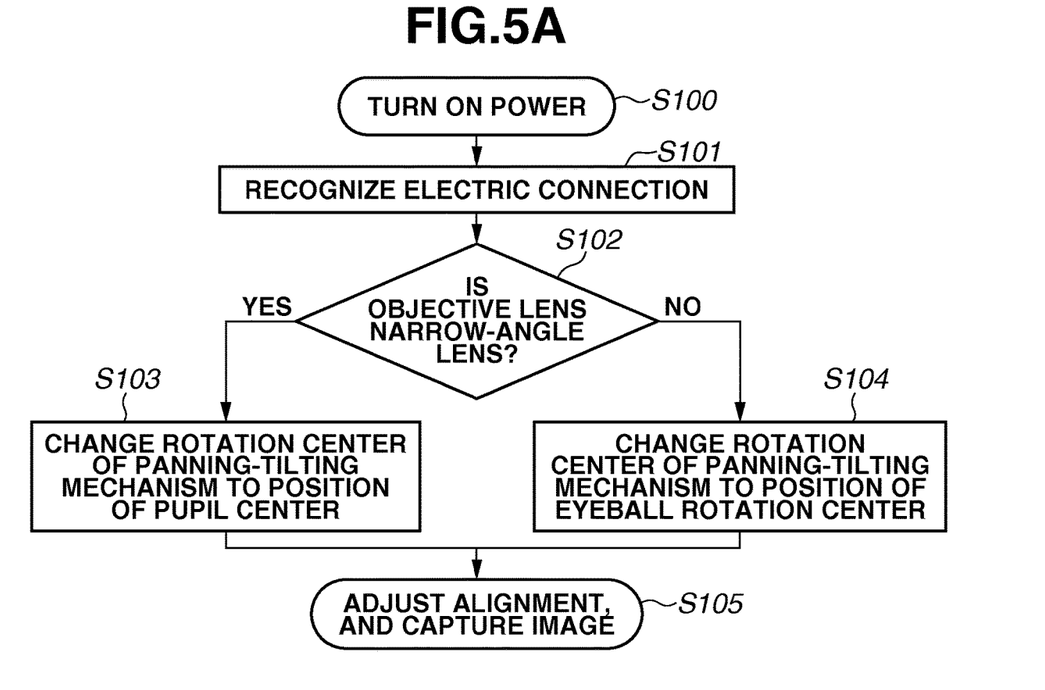
FIGS. 5A and 5B are flowcharts illustrating processing flows for moving a panning-tilting mechanism of the ophthalmologic imaging apparatus according to the first exemplary embodiment.
Figure 5B:
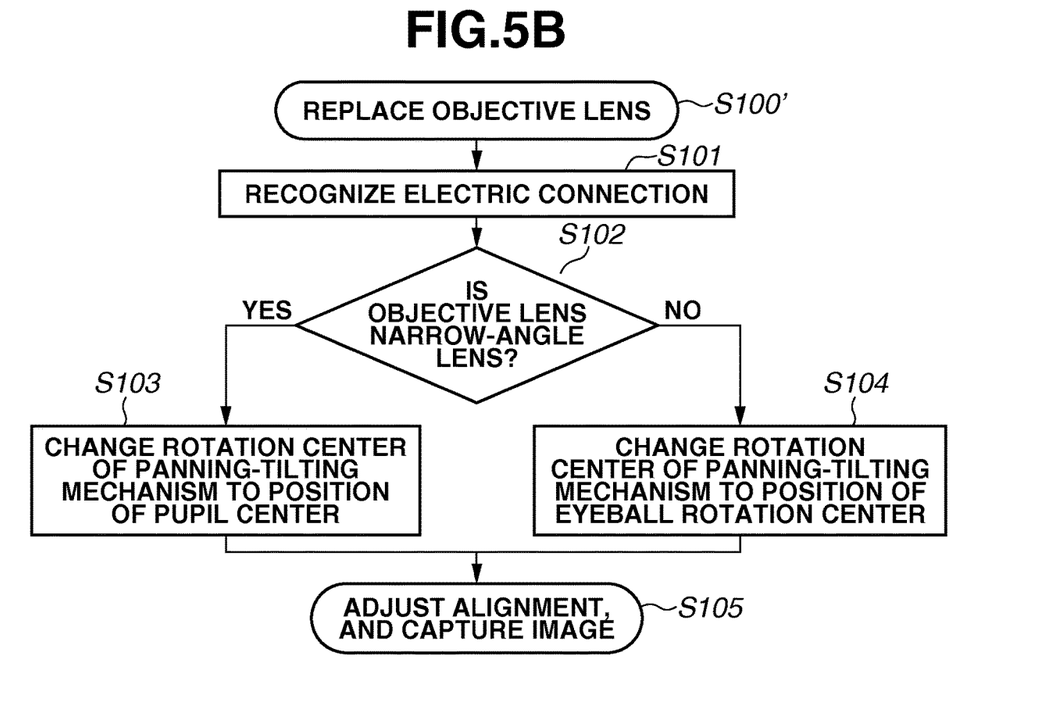

Processing for controlling the position of the rotation center of the panning-tilting mechanism will be described with reference to FIGS. 5A and 5B. FIG. 5A is a flowchart illustrating processing for automatically controlling and changing the rotation center of the panning-tilting mechanism executed by the control unit when the examiner turns on the power of the apparatus. In step S100, the examiner turns on the power of the apparatus. When the examiner turns on the power of the apparatus, in step S101, the control unit recognizes the electrical connection established between the connection terminal 22 provided on the optical system main unit 6 and the coupling portion 21a of the lens barrel 21. In step S102, the control unit automatically recognizes a type of the objective lens 10. When the type of the objective lens 10 is the narrow-angle lens (YES in step S102), the processing proceeds to step S103. In step S103, the control unit drives the motor 19 to move the rotation center of the panning-tilting mechanism to the position of the pupil center. On the other hand, when the type of the objective lens 10 is a wide-angle lens (NO in step S102), the processing proceeds to step S104. In step S104, the control unit drives the motor 19 to move the rotation center of the panning-tilting mechanism to the position of the eyeball rotation center. Then, in step S105, based on an instruction of the examiner, the alignment of the optical system main unit 6 with respect to the subject's eye 16 is adjusted and an image of the eye fundus of the subject's eye 16 is captured. The same automatic control processing as described above will be executed when the objective lens 10 is replaced while the power of the apparatus is turned on. FIG. 5B is a flowchart illustrating processing that is to be executed when the objective lens 10 is replaced. After the objective lens 10 is replaced in step S100', similar to the above-described processing flow, the control unit automatically controls and changes the position of the rotation center of the panning-tilting mechanism according to the type of objective lens 10.

Figure 6B:
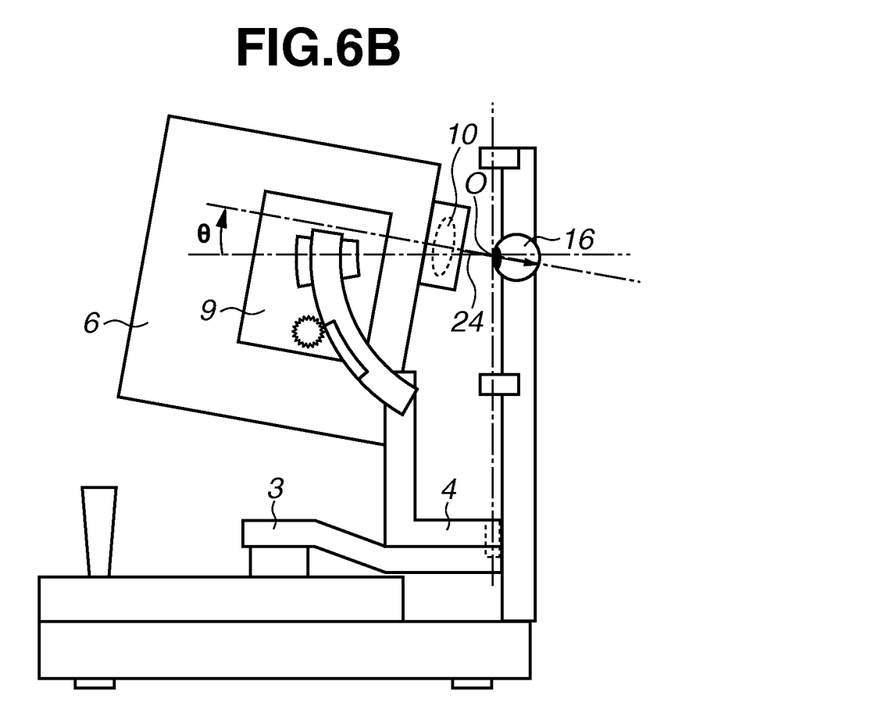

Further, an ophthalmologic imaging operation in a pupil center panning-tilting mode will be described with reference to FIGS. 6A and 6B. Each of FIGS. 6A and 6B illustrates a state where the optical system main unit 6 and the subject's eye 16 are arranged to have an appropriate operation distance between the objective lens 10 and the subject's eye 16 in the pupil center panning-tilting mode. At this time, the optical system main unit 6 and the movable plate 9 are arranged in a positional relationship illustrated in FIG. 3A, so that the examiner can perform the panning-tilting operation while maintaining an appropriate distance between the optical system 6 and the subject's eye 16. When the optical axis direction of the objective lens 10 is horizontal as illustrated in FIG. 6A, SLO measurement light 24 (indicated by a black arrow in FIG. 6A) penetrating through the objective lens 10 passes through the pupil center of the subjects' eye 16, so that a substantially central portion of the eye fundus is irradiated therewith. On the other hand, as illustrated in FIG. 6B, when the examiner performs the depression-elevation operation of the optical system main unit 6 to incline the optical axis of the objective lens 10 by a θ-degree with respect to the optical axis in the horizontal direction, a position different from the substantially central portion of the eye fundus of the subject's eye 16 is irradiated with the SLO measurement light 24. As described above, the examiner performs the panning-tilting operation of the optical system main unit 6 and scans the subject's eye 16 with the SLO measurement light 24 by making the pupil center thereof as the rotation center in order to capture a desired region in the eye fundus.

Figure 3B:
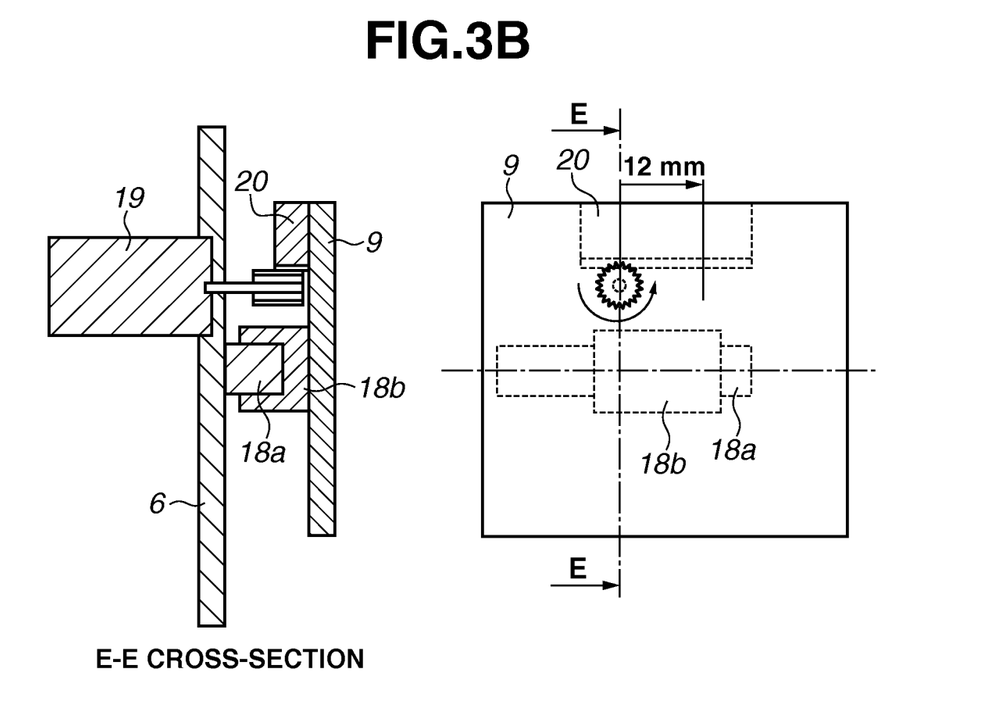
Figure 7B:
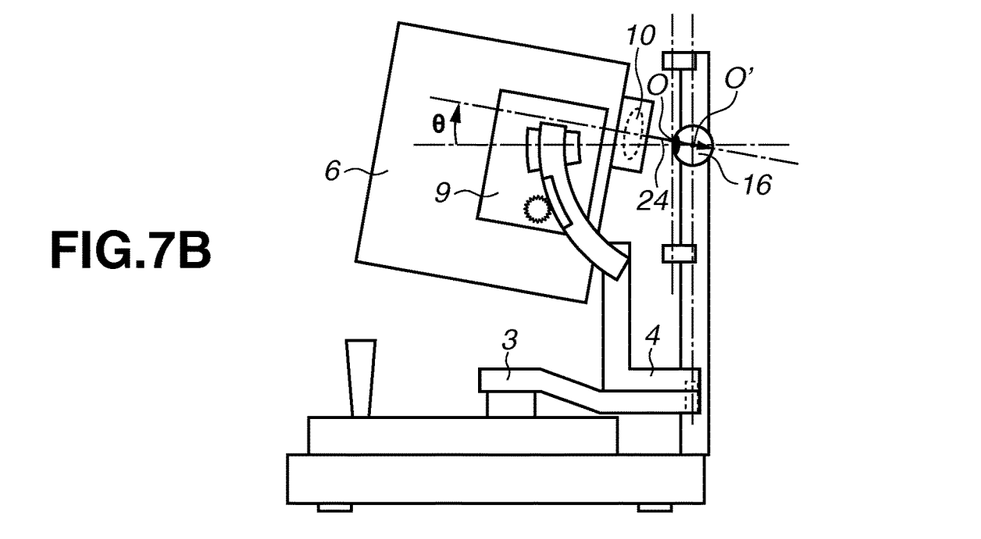
Figure 7C:
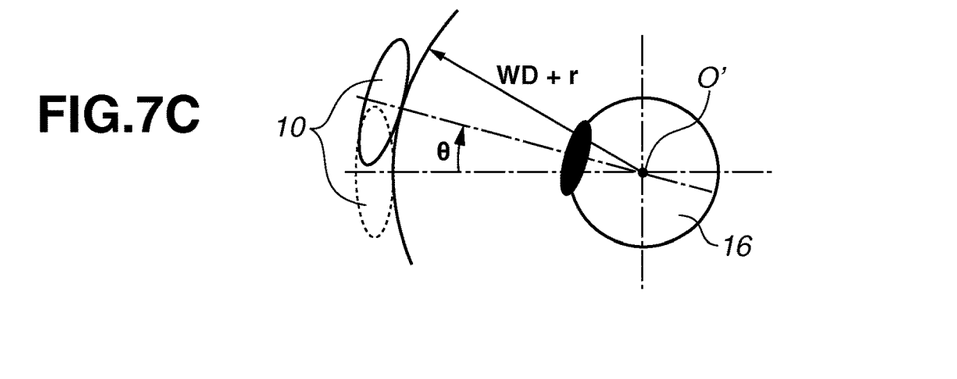

Further, an ophthalmologic imaging operation in an eyeball rotation center panning-tilting mode will be described with reference to FIGS. 7A to 7C. In the eyeball rotation center panning-tilting mode, the rotation center of the panning-tilting operation is moved to the eyeball rotation center O' of the subject's eye 16. Therefore, even if the axis of the subject's eye 16 is misaligned in a measurement period, the examiner can easily make an adjustment on the alignment again by panning or tilting the optical system main unit 6. Each of FIGS. 7A and 7B illustrates a state where the optical system main unit 6 and the subject's eye 16 are arranged at an appropriate distance in the eyeball rotation center panning-tilting mode. At this time, the optical system main unit 6 and the movable plate 9 are arranged in a relative positional relationship as illustrated in FIG. 3B. When the optical axis direction of the objective lens 10 is horizontal as illustrated in FIG. 7A, similar to the state illustrated in FIG. 6A, the SLO measurement light 24 passes through the objective lens 10 and the pupil center of the subject's eye 16, so that the substantially central portion of the eye fundus is irradiated therewith. In comparison to the case where the narrow-angle lens is used, a wide region in the eye fundus can be captured as a single image when the wide-angle lens is used. Therefore, when the examiner irradiates a desired portion of the eye fundus with the SLO measurement light 24, the necessity of panning or tilting the optical system main unit 6 is reduced.

In a case where the visual fixation of the subject's eye 16 is not stable, the axis of the eye may be moved by an unintended eye movement of the subject after the examiner has adjusted the operation distance and the focus between the optical system main unit 6 and the subject's eye 16, so that the SLO measurement light 24 may be emitted to a position shifted from a desired irradiation portion of the eye fundus. FIG. 7B is a diagram illustrating a state where the optical system main unit 6 is tilted and adjusted to an inclination angle θ-degree of the axis of the subject's eye 16. As illustrated in FIG. 7C, in the eyeball rotation center panning-tilting mode, a rotation radius of the objective lens 10 in the panning-tilting operation is a sum of an operation distance WD between the subject's eye 16 and the objective lens 10, and a distance "r" between the pupil center and the eyeball rotation center of the subject's eye 16. Therefore, when the examiner pans or tilts the optical system main unit 6 to make the optical axis of the objective lens 10 substantially conform to the axis of the subject's eye 16, relative positions of the optical system main unit 6 and the subject's eye 16 can be maintained at an appropriate distance. Therefore, even if the axis of the subject's eye is misaligned, the examiner can easily readjust the alignment thereof by simply panning or tilting the optical system main unit 6.

Further, a manual operation for switching a position of the movable plate 9 will be described. The pupil center panning-tilting mode and the eyeball rotation center panning-tilting mode can be switched by using a switching button disposed at the platform 2. Although the tilting operation has been described as the above, the same can be also said for the panning operation.

<Mechanism for Switching Plurality of Rotation Centers>

Figure 8:
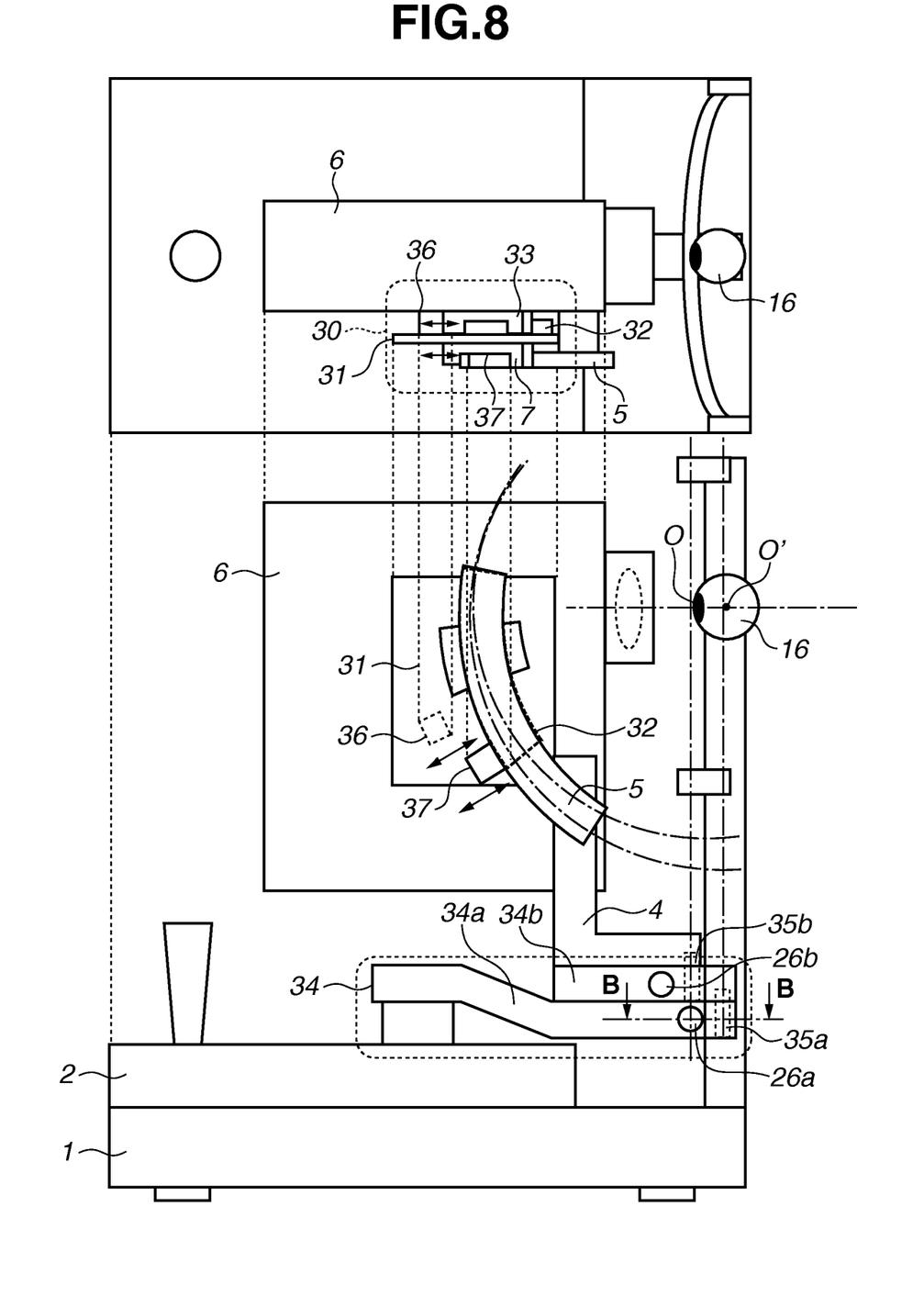
FIG. 8 is a diagram illustrating a configuration of an ophthalmologic imaging apparatus according to a second exemplary embodiment.

Subsequently, a second exemplary embodiment will be described with reference to FIG. 8. FIG. 8 is a diagram illustrating a configuration of an SLO according to the present exemplary embodiment. An arm holding member 34 is attached to the base plate 1 of the SLO via the platform 2. The first arc-shape guiding member 5 as an example of the first rotation unit is fixed to the arm holding member 34 via the arm 4.

First, a switching mechanism for switching the rotation centers in the right-left direction will be described. The arm holding member 34 is configured of an arm holding member 34a attached to the platform 2, and an arm holding member 34b as an example of the second rotation unit. The arm holding members 34a and 34b are rotatably attached to each other via a shaft 35a, whereas the arm holding member 34b and the arm 4 as an example of the first rotation unit are rotatably attached to each other via a shaft 35b. A right-left rotation stopper 26a as an example of the switching unit that suppresses the rotation of the arm holding member 34b in the right-left direction with respect to the arm holding member 34a is attached to the arm holding member 34a, whereas a right-left rotation stopper 26b as an example of the switching unit that suppresses the rotation of the arm 4 in the right-left direction with respect to the arm holding member 34b is attached to the arm holding member 34b.

Figure 9A:
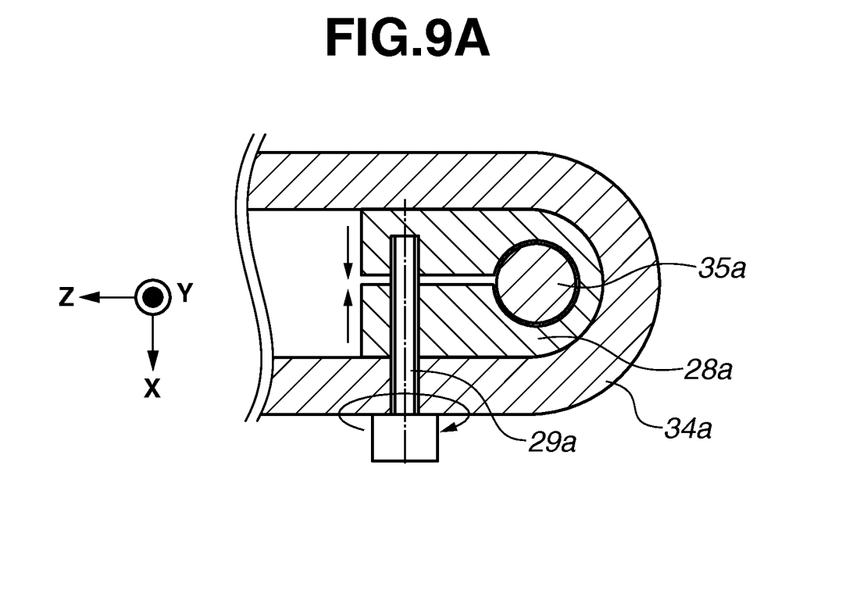
FIGS. 9A and 9B are cross-sectional diagrams illustrating a suppression mechanism for suppressing the rotation in a horizontal direction of the ophthalmologic imaging apparatus according to the second exemplary embodiment.
Figure 9B:
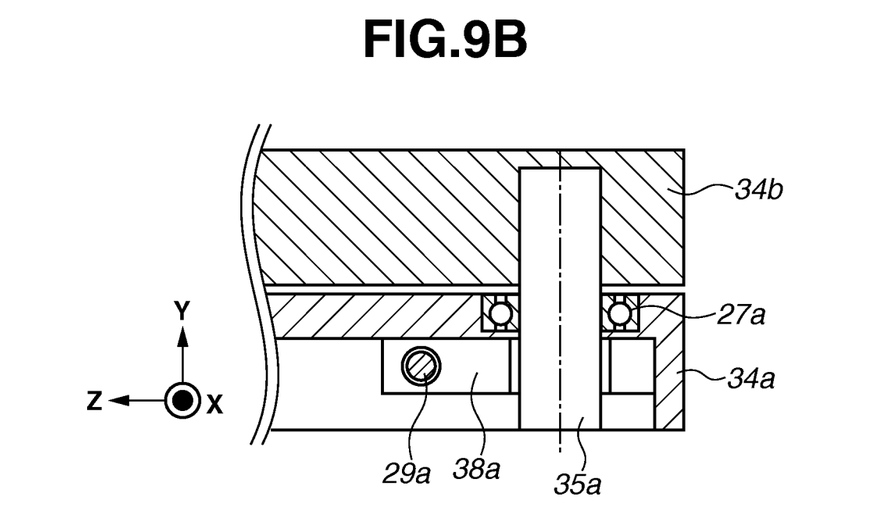

FIGS. 9A and 9B are diagrams illustrating a mechanism of the right-left rotation stopper 26a (26b). FIG. 9A is a cross-sectional diagram taken along a line B-B in FIG. 8, and FIG. 9B is a cross-sectional diagram viewed in a +X direction, illustrating an YZ plane that passes the central axis of the shaft 35a in FIG. 8. The shaft 35a is fixed to the arm holding member 34b. A bearing 27a for holding the shaft 35a, a U-shape stopper 28a for stopping the rotation of the arm holding member 34a, and a hand screw 29a for tightening the U-shape stopper 28a are attached to the arm holding member 34a. By tightening or loosening the hand screw 29a, the examiner can switch whether to fix or rotate the shaft 35a. When the apparatus is operated, at least any one of the right-left rotation stoppers 26a and 26b is fixed.

The shaft 35a and the shaft 35b are separated from each other by a distance of 12 mm on the optical axis direction of the objective lens 10. As illustrated in FIG. 8A, when the objective lens 10 and the subject's eye 16 are arranged at an appropriate operation distance, the central axis of the shaft 35a passes through the eyeball rotation center O' of the subject's eye 16 (i.e., first rotation center), and the central axis of the shaft 35b passes through the pupil center O (i.e., second rotation center). Therefore, axes of the rotation center in the right-left direction of the optical system main unit 6 can be switched in such a manner that the rotation center thereof is the substantial pupil center O of the subject's eye 16 when the rotation about the shaft 35a is suppressed by the right-left rotation stopper 26a, whereas the rotation center thereof is the eyeball rotation center O' of the subject's eye 16 when the rotation about the shaft 35b is suppressed by the right-left rotation stopper 26b.

A mechanism for switching the rotation radiuses in the depression-elevation direction according to the change in the rotation center in the right-left direction will be described. The first arc-shape guiding member 5 is a curved guide rail. A switching mechanism 30 that switches the rotation radiuses in the depression-elevation direction of the optical system main unit 6 according to the change in the rotation center in the right-left direction is disposed at a position between the optical system main unit 6 and the first arc-shape guiding member 5.

By switching the rotation radiuses of the tilting operation according to the axis position of the rotation center of the panning operation, the examiner can tilt the optical system main unit 6 while maintaining an appropriate distance between the optical system main unit 6 and the subject's eye 16.

The switching mechanism 30 for switching the rotation radiuses of the tilting operation is configured of the first arc-shape guiding member 5, the guide block 7 for holding the first arc-shape guiding member 5, a guide block fixing plate 31 fixed to the guide block 7 configured to move along the first arc-shape guiding member 5, a second arc-shape guide 32 as an example of the second rotation unit, fixed to a surface of the guide block fixing plate 31 opposite to the guide block 7, and a second guide block 33 for holding the second arc-shape guiding member 32. The second guide block 33 is attached to a side surface of the optical system main unit 6. Further, a stopper 36 that suppresses the movement in a depression-elevation direction is attached to the side surface of the optical system main unit 6 in order to prevent the optical system main unit 6 from moving along the second arc-shape guiding member 32. A stopper 37 that suppresses the movement in the depression-elevation direction is attached to the side surface of the guide block fixing plate 31 in order to prevent the guide block fixing plate 31 from moving along the first arc-shape guiding member 5. The stoppers 36 and 37 are movable in directions indicated by black arrows in FIG. 8. By pressing the stopper 36 against the side surface of the second arc-shape guiding member 32, the examiner can suppress the movement of the optical system main unit 6 along the second arc-shape guiding member 32. On the other hand, by pressing the stopper 37 against the side surface of the first arc-shape guiding member 5, the examiner can suppress the movement of the guide block fixing plate 31 along the first arc-shape guiding member 5.

At this time, the rotation center of the first arc-shape guiding member 5 is a point O' (i.e., first rotation center) positioned on the optical axis of the objective lens 10 and the central axis of the shaft 35a, whereas the rotation center of the second arc-shape guiding member 32 is a point O (i.e., second rotation center) positioned on the optical axis of the objective lens 10 and the central axis of the shaft 35b. In other words, the rotation center of the first arc-shape guiding member 5 is away from the optical system main unit 6 farther than the rotation center of the second arc-shape guiding member 32. At this time, the rotation radius of the first arc-shape guiding member 5 is longer than the rotation radius of the second arc-shape guiding member 32. Further, when the examiner uses the stopper 36, the optical system main unit 6 can be depressed or elevated along the substantial pupil center of the subject's eye 16. Furthermore, when the examiner uses the stopper 37, the optical system main unit 6 can be depressed or elevated along the eyeball rotation center of the subject's eye 16.

According to the above-described exemplary embodiment, the examiner can switch the rotation centers of the panning-tilting operation between the eyeball rotation center and the pupil center while maintaining the appropriate operation distance between the apparatus main body and the subject's eye. In a case where an image of the eye fundus of the subject's eye with unstable visual fixation is to be captured, the examiner can easily adjust the alignment thereof by panning or tilting the optical system main unit. When the rotation center for panning or tilting the optical system main unit of the apparatus is the substantially pupil center of the subject's eye, the examiner can observe a desired region of the eye fundus of the subject's eye by performing the panning-tilting operation. On the other hand, in a case where the rotation center for panning or tilting the optical system main unit is the eyeball rotation center of the subject's eye, the examiner can adjust the optical axis of the measurement light to the substantially axis of the subject's eye by simply panning or tilting the optical system main unit even if fixation disparity or rotation occurs in the subject's eye, so that the alignment thereof can be readjusted easily.

Further, the present invention can be realized by executing the following processing. In other words, software (a program) for realizing the function of the above-described exemplary embodiment is supplied to a system or an apparatus via a network or various storage media, so that a computer (or a central processing unit (CPU) or a micro processing unit (MPU)) of the system or the apparatus reads and executes the program.

OTHER EMBODIMENTS

Additional embodiments can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that these exemplary embodiments are not seen to be limiting. The scope of the following claims is to be accorded the broadest interpretation so as to encompass all such modifications and equivalent structures and functions.

This application claims the benefit of Japanese Patent Application No. 2014-210837, filed Oct. 15, 2014, which is hereby incorporated by reference herein in its entirety.

What is claimed is:

1. An ophthalmologic imaging apparatus comprising:
a housing configured to include an optical system that irradiates a subject's eye with measurement light and receives returning light returned from the subject's eye irradiated with the measurement light;
a rotation unit configured to rotate the housing by moving the housing along an arc-shaped guiding member with respect to a rotation center as a predetermined position on an optical axis of the optical system;
a guide holding member configured to hold the arc-shape guiding member;
a position changing unit configured to change a position of the rotation center along a first direction on the optical axis of the optical system by moving a platform with respect to a base plate, the platform is capable of integrally moving with the arc-shaped guiding member; and
a positional relationship holding unit disposed at a position between the housing and the arc-shaped guiding member and configured to move the housing along a second direction opposite to the first direction with respect to the positional changing unit without using the platform and the rotation unit, so as to hold a positional relationship between the housing and the subject's eye,
wherein the rotation unit is configured to rotate the housing by moving the housing, the guide holding member, and the positional relationship holding unit integrally along the arc-shaped guiding member.

2. The ophthalmologic imaging apparatus according to claim 1, wherein the guide holding member is disposed at a position between the housing and the arc-shaped guiding member, and includes a mechanism for moving the housing with respect to the rotation unit.

3. The ophthalmologic imaging apparatus according to claim 2, wherein the guide holding member further includes a driving unit configured to drive the housing in a direction in which a distance between the housing and the subject's eye is changed, and a control unit configured to control, according to the change in the position of the rotation center, the driving unit to drive the housing in the direction opposite to the direction in which the position of the rotation center is changed.

4. The ophthalmologic imaging apparatus according to claim 1, wherein the position changing unit includes a mechanism for moving the rotation center with respect to a base plate.

5. The ophthalmologic imaging apparatus according to claim 1,
wherein the rotation center is a pupil center of the subject's eye in a narrow-angle image capturing mode, and
wherein the rotation center is an eyeball rotation center of the subject's eye in a wide-angle image capturing mode.

6. The ophthalmologic imaging apparatus according to claim 1,
wherein the rotation unit includes a first rotation unit configured to rotate the housing about a first rotation center on the optical axis of the optical system, and a second rotation unit configured to rotate the housing about a second rotation center on the optical axis of the optical system, and
wherein the position changing unit changes the position of the rotation center by switching the rotation units between the first rotation unit and the second rotation unit.

7. The ophthalmologic imaging apparatus according to claim 6, wherein a rotation radius of the first rotation unit is longer than a rotation radius of the second rotation unit.

8. The ophthalmologic imaging apparatus according to claim 6, wherein the first rotation center is positioned away from the housing farther than the second rotation center.

9. The ophthalmologic imaging apparatus according to claim 6,
wherein the first rotation center is an eyeball rotation center of the subject's eye, and
wherein the second rotation center is a pupil center of the subject's eye.

10. An ophthalmologic imaging apparatus comprising:
a housing configured to include an optical system that irradiates a subject's eye with measurement light and receives returning light returned from the subject's eye irradiated with the measurement light;
a rotation unit configured to rotate the housing by moving the housing along an arc-shaped guiding member with respect to a rotation center as a predetermined position on an optical axis of the optical system;
a guide holding member configured to hold the arc-shaped guiding member;
a driving unit disposed at a position between the housing and the arc-shaped guiding member and configured to drive the housing in a direction in which a distance between the housing and the subject's eye is changed with respect to the arc-shaped guiding member;
a position changing unit configured to change a position of the rotation center on the optical axis of the optical system by moving the housing with respect to the subject's eye; and
a control unit configured to control, according to the change in the position of the rotation center of the rotation unit, the driving unit to drive the housing in a direction opposite to a direction in which the position of the rotation center is changed,
wherein the rotation unit is configured to rotate the housing by moving the housing, the guide holding member, and the driving unit integrally along the arc-shaped guiding member.

11. The ophthalmologic imaging apparatus according to claim 10, wherein the position changing unit includes a mechanism for moving the rotation center with respect to a base plate.

12. The ophthalmologic imaging apparatus according to claim 10,
wherein the rotation center is a pupil center of the subject's eye in a narrow-angle image capturing mode, and
wherein the rotation center is an eyeball rotation center of the subject's eye in a wide-angle image capturing mode.

13. The ophthalmologic imaging apparatus according to claim 10,
wherein the rotation unit includes a first rotation unit configured to rotate the housing about a first rotation center on the optical axis of the optical system, and a second rotation unit configured to rotate the housing about a second rotation center on the optical axis of the optical system, and wherein the position changing unit changes the position of the rotation center by switching the rotation units between the first rotation unit and the second rotation unit.

14. The ophthalmologic imaging apparatus according to claim 13, wherein a rotation radius of the first rotation unit is longer than a rotation radius of the second rotation unit.

15. The ophthalmologic imaging apparatus according to claim 13, wherein the first rotation center is positioned away from the housing farther than the second rotation center.

16. The ophthalmologic imaging apparatus according to claim 13, wherein the first rotation center is an eyeball rotation center of the subject's eye, and wherein the second rotation center is a pupil center of the subject's eye.

* * * * *